US010836986B2

(12) United States Patent
Roosloot et al.

(10) Patent No.: US 10,836,986 B2
(45) Date of Patent: Nov. 17, 2020

(54) BIOREACTOR SYSTEM AND SINGLE-USE CELL CULTURE CONTAINER FOR USE THEREIN

(71) Applicant: SCINUS CELL EXPANSION B.V., Bilthoven (NL)

(72) Inventors: Emerentius Gerardus Roosloot, Bilthoven (NL); Rudolf Hendrikus Jozef Das, Bilthoven (NL); Joost Dick De Bruijn, Bilthoven (NL); Pieter Theo Elias Van Santen, Bilthoven (NL)

(73) Assignee: SCINUS CELL EXPANSION B.V., Bilthoven (NL)

( * ) Notice: Subject to any disclaimer, the term of this patent is extended or adjusted under 35 U.S.C. 154(b) by 446 days.

(21) Appl. No.: 14/903,582

(22) PCT Filed: Jul. 18, 2014

(86) PCT No.: PCT/NL2014/050490
§ 371 (c)(1),
(2) Date: Jan. 7, 2016

(87) PCT Pub. No.: WO2015/009153
PCT Pub. Date: Jan. 22, 2015

(65) Prior Publication Data
US 2016/0152935 A1 Jun. 2, 2016

(30) Foreign Application Priority Data
Jul. 18, 2013 (NL) ...................................... 2011189

(51) Int. Cl.
*C12M 1/00* (2006.01)
*C12M 3/06* (2006.01)
(Continued)

(52) U.S. Cl.
CPC ............ *C12M 23/14* (2013.01); *C12M 23/26* (2013.01); *C12M 23/28* (2013.01); *C12M 27/16* (2013.01);
(Continued)

(58) Field of Classification Search
CPC ........... A23K 40/00; A23K 50/40; A23L 3/01; A23L 3/364; A23L 3/40; C12M 23/14;
(Continued)

(56) References Cited

U.S. PATENT DOCUMENTS 5,057,429 A 10/1991 Watanabe et al.
5,309,180 A * 5/1994 Uchida ................ B41J 2/17596
347/30
(Continued)

FOREIGN PATENT DOCUMENTS

JP 3-7575 1/1991
JP 3-10676 1/1991
WO WO-2011142670 A1 * 11/2011 ............ C12M 23/14

OTHER PUBLICATIONS

International Search Report for PCT/NL2014/050490, dated Sep. 26, 2014, 3 pages.

*Primary Examiner* — Gautam Prakash
*Assistant Examiner* — Lydia Edwards
(74) *Attorney, Agent, or Firm* — Morrison & Foerster LLP (57) ABSTRACT

A bioreactor system (1A; 1B) includes a variable volume container (3) having a flexible outer wall (27, 29) defining a cell-culture chamber for containing a fluid culture medium, and anchorage dependent cells in suspension. A agitator unit of the system (1A; 1B) is in fluid communication with first, second and third fluid ports (43, 45, 47A; 47B) for performing controlled replenishment of the culture medium in the cell-culture chamber, to admit fresh nutritive
(Continued)

culture medium into the cell-culture chamber and for allowing draining of waste culture medium from the cell-culture chamber. The agitator unit further has a roller (15) for pinching the outer wall of the variable volume container (3) to thereby increase its a volume that forms the cell-culture chamber, starting from the initial minimum volume area (23), and means for gently agitating the cell-culture chamber.

14 Claims, 8 Drawing Sheets

(51) Int. Cl.
    *C12M 1/36* (2006.01)
    *C12M 1/34* (2006.01)
(52) U.S. Cl.
    CPC ............ *C12M 29/04* (2013.01); *C12M 29/10* (2013.01); *C12M 41/44* (2013.01)

(58) Field of Classification Search
    CPC ...... C12M 23/26; C12M 23/28; C12M 27/16; C12M 29/04; C12M 29/10; C12M 41/44; Y10S 426/805
    See application file for complete search history.

(56) References Cited

U.S. PATENT DOCUMENTS

| | | |
|---|---|---|
| 6,060,306 A | 5/2000 | Flatt et al. |
| 2013/0157353 A1* | 6/2013 | Dijkhuizen Borgart ..................... C12M 23/14 435/297.2 |
| 2013/0157355 A1* | 6/2013 | Barrett ................... C12M 23/14 435/325 |

* cited by examiner

BIOREACTOR SYSTEM AND SINGLE-USE CELL CULTURE CONTAINER FOR USE THEREIN

CROSS-REFERENCE TO RELATED APPLICATIONS

This application is the national phase of PCT application PCT/NL2014/050490 having an international filing date of 18 Jul. 2014, which claims benefit of Dutch patent application No. 2011189 filed 18 Jul. 2013. The contents of the above patent applications are incorporated by reference herein in their entirety.

The invention relates to a bioreactor system that includes an agitator apparatus and at least one single-use cell culture container. The single-use cell culture container thereby preferably is in the form of a disposable cell-culture-bag, while the agitator apparatus, which can also be associated with a perfusion device, is designed for repeated use.

In general such a bioreactor system is described in patent document U.S. Pat. No. 5,057,429. In the apparatus according to this patent document animal cells are floated in a double-bag container, wherein an outer bag contains a fluid culture medium and a volume of air, while an inner bag contains cells suspended in a fluid culture medium. The inner and outer bags are separated by a semi-permeable membrane that allows transfer of the fluid culture medium and air to the inner bag. To promote the exchange of nutrients between the outer and inner bags the double-bag container is brought into motion by an agitator.

To cultivate cells in a bioreactor the cells need a specific environment, such as a fluid culture medium with a constant optimal temperature, pH and concentration of dissolved oxygen (DO). Part of this environment is created by excretion of components by the cells itself. If the volume of the bioreactor is too large compared to the amount of cells, these compounds are diluted below the effective concentration, with the result that the cells don't grow. The cells to be cultured may be any kind of cells, such as bacterial cells, Fungi, yeast cells, plant cells, algae, insect cells, mammalian cells. In a preferred embodiment of the invention and/or embodiments thereof the cells are mammalian cells, more preferably human cells, more preferably progenitor cells, more preferably stem cells, however the cells may also be chosen from embryonic cells, skin cells, kidney cells, pancreas cells, liver cells, red blood cells, white blood cells, bone cells, cartilage cells, muscle cells, lung cells, eye cells, ovary cells, omnipotent cells, pluripotent cells, cancer cells. The cells may be primary cells but may also be from a cell-line. The cells may be grown in suspension but may also be adherent dependent and require growth for example on scaffolds or microcarriers.

It has been tried to cultivate shear sensitive cells, such as mammalian cells, in particular human cells, and more in particular human stem cells in bioreactor containers that have both a liquid phase and a gas phase ($CO_2$ and $O_2$) to control the dissolved oxygen (DO) and pH of the fluid medium. The presence of a gas phase introduces bubbles in the medium. These bubbles introduces shear forces, which are harmful for shear stress sensitive cells. An even more important drawback is that the known bioreactor containers have a fixed volume, which does not allow expansion of the container volume to promote cell cultivation at reduced shear stress.

Accordingly it is an object of the present invention to propose an improved bioreactor system and single-use cell culture container for use therein. In a more general sense it is thus an object of the invention to overcome or ameliorate at least one of the disadvantages of the prior art. It is also an object of the present invention to provide alternative structures which are less cumbersome in assembly and operation and which moreover can be made cost effective. Alternatively it is an object of the invention to at least provide the public with a useful alternative.

To this end the present invention envisions a solution to this problem by providing a bioreactor system and a single-use cell culture container, which makes it possible to start with a small liquid volume in the bioreactor and expand the volume during the cultivation of the cells so that the concentration of the secreted products stays above the critical level which is needed for an optimal cell growth.

In particular the present invention provides a variable volume bioreactor container for culturing anchorage dependent animal or human cells, in particular human stem cells, in a bioreactor system. The variable volume container comprising: a flexible outer wall defining a cell-culture chamber for containing a fluid cell culture medium; a first edge for removable attachment to a support of an agitator unit of the bioreactor system; a second edge—parallel to and spaced from the first edge—for removable attachment to one of a cylindrical roller and a support of the agitator unit; a minimum volume area of the container being defined adjacent to the first edge; a first fluid port in the minimum volume area connectable to the agitator unit of the system for adding and removing cells, microcarriers and cell culture medium; a second fluid port in the minimum volume area connectable to the agitator unit for removing gas; a third fluid port in the minimum volume area connectable to the agitator unit; and at least one filter associated with the third fluid port to ensure that the third port enables sampling of the fluid cell culture medium while retaining any microcarriers and adherent cells in the cell culture chamber. Such a variable volume bioreactor container allows expansion of the container volume to promote cell cultivation at reduced shear stress. It further also allows elimination of an excessively large head space and gaseous phase from the bioreactor container. According to a further aspect of the invention, the variable volume bioreactor container further comprises at least one sensor. The at least one sensor is advantageously adapted to measure at least one of pH, dissolved oxygen, and at least one parameter related to biomass. Also advantageously the at least one sensor is located in the minimum volume area.

Advantageously the cell-culture chamber has a minimum volume area of between 25-150 mL (millilitres) and a virtually unlimited maximum volume. Cell culture chambers of 20 L and even 700 L are not at all unrealistic. A size range starting from such a minimum volume was found to give good results in optimizing yield. The at least one filter is advantageously arranged to allow passage of suspension cells and for blocking passage of plurality of microcarriers and stem cells from the at least one outlet. Thereby the at least one filter preferably has a mesh size adapted to keep at least a majority of microcarriers in. With a commonly used size of microcarriers this can, for example, be a mesh size not exceeding 60 µm (micrometer). It is also advantageous for the at least one filter to have an area of at least 7 $cm^2$, and preferably of at least 36 $cm^2$.

In the variable volume bioreactor container according to the present invention also advantageously at least one of the first, second and third fluid ports includes a tube for connecting to a perfusion device associated with the agitator unit of the system. Having tubular extensions to the fluid ports enhances manipulation of the bioreactor container when connecting or disconnecting it from the agitator unit of the system.

Advantageously the flexible outer wall is made of a sheet of substantially gas impermeable material. Ensuring that the container wall is substantially impermeable to gas prevents inaccuracies in the gas control.

The variable volume container is advantageously in the form of a flexible bag, and more advantageously also designed for single-use. Such a variable volume container can be discarded after use and replaced by a new sterile one to exclude any risk of cross-contamination between cultures. Such a variable volume container is advantageously a single-use plastic bag, which can be economically produced in large numbers, without the material costs becoming prohibitive. It is also advantageous for the flexible outer wall to include a flexible plastic foil. The flexible outer wall is advantageously made from a polymer material consisting of one of EVE, PE and PVC.

The second edge of the variable volume bioreactor container is also advantageously provided with a pocket for receiving a rod.

According to a further aspect the invention also relates to a bioreactor system for culturing anchorage dependent animal cells in a microcarrier suspension. The system according to the invention, or at least according to the present disclosure, includes: a variable volume container having a flexible outer wall defining a cell-culture chamber for containing a fluid culture medium, as defined herein above, and an agitator unit with at least one inlet in fluid communication with the third fluid port and at least one outlet in fluid communication with the first fluid port for performing controlled replenishment of the culture medium in the cell-culture chamber. The agitator unit thereto has at least one inlet for fluid communication with the cell-culture chamber and adapted to admit fresh nutritive culture medium into the cell-culture chamber, and at least one outlet for fluid communication with the cell-culture chamber and adapted to allow draining of waste culture medium from the cell-culture chamber with a filter retaining microcarriers within the cell culture chamber. The agitator unit, which also is effective as a volume expansion unit is further also equipped with means for pinching the outer wall of the variable volume container to create a partially flattened section and being operable for increasing the cell-culture chamber in volume by decreasing the flattened section. Agitating means are also associated with the agitator and expansion unit for gently agitating the cell-culture chamber in combination with control means for periodically performing seeding, agitation and pinching, harvesting, and collecting of cultured cell material. Such a bioreactor system allows an optimal use of the above defined variable volume bioreactor container. Advantageously a plurality of preferably identical microcarriers are suspended in the culture medium contained in the cell-culture chamber. Also advantageously the fluid communication between the agitator and expansion unit and the cell-culture chamber is disconnectable to allow easy exchange and single use of the bioreactor container.

The means for pinching the outer wall of the variable volume container preferably includes a transferable cylindrical roller arranged for rotation and to contact a surface of the outer wall of the variable volume container. In this regard the means for pinching preferably also includes a plate member defining a substantially flat support surface for supporting a portion of the outer wall surface of the variable volume container opposite to the cylindrical roller. It is further advantageous when the cylindrical roller is adapted to be urged toward the plate member to exert pressure on a portion of the variable volume container extending between the cylindrical roller and the support member. Preferably urging of the cylindrical roller toward the plate member is by resilient spring means, and the resilient spring means is adjustable in tension. In a particularly advantageous arrangement the resilient spring means include compression springs acting on opposite ends of a bearing shaft about which the cylindrical roller is arranged for rotation. In a bioreactor system including the cylindrical roller this roller may also be adapted to receive and clamp a portion of the flexible bag adjoining the second edge.

A bioreactor system according to the invention may also have the substantially flat support surface of the plate member covered by a resiliently compressible or deformable material, such as a silicon or other elastomeric layer on a surface facing the cylindrical roller to equally distribute pressure exerted by the cylindrical roller and to obtain an increased contact surface on the flexible bag. In such an embodiment the variable volume container is preferably in the form of a flexible bag, and the first edge of the flexible bag is attached to a support positioned at a distance perpendicular to the plate member for retaining the first edge of the flexible bag in parallel to the support surface of the plate member. Then the second edge of the flexible bag, opposite to the first end, is either held to the plate member, or to a circumferential perimeter surface defined by the cylindrical roller.

When the second edge of the flexible bag, opposite to the first end, is held to a circumferential perimeter surface of the cylindrical roller, it is advantageous when the cylindrical roller defines an axial slot in its circumferential perimeter surface for receiving the second edge. The slot then advantageously defines an undercut elongate chamber for receiving a rod encapsulated in a pocket along the second edge of the variable volume container.

Also when the second edge of the flexible bag is held to a circumferential perimeter surface of the cylindrical roller, the cylindrical roller may advantageously be axially sectioned in two halves, so as to clamp the second edge there between.

When the means for pinching includes a transferable cylindrical roller, to which the second edge of the flexible bag is optionally held, it is further advantageous when the volume of the cell-culture chamber is increased by gradually unwinding the flexible bag from the cylindrical roller surface. To this end the bearing shaft, about which the cylindrical roller is arranged for rotation, is itself advantageously arranged for controlled movement in parallel to and away from the first edge of the flexible bag for increasing the volume of the cell-culture chamber defined by the flexible bag.

A bioreactor system according to the invention may advantageously be used with a variable container formed as a flexible bag that is adapted to be increased in volume from 10 mL to a much larger volume. More in particular the flexible bag is adapted to be increased in volume starting at 100 mL.

At a seeding stage the cell-culture chamber is adapted to be kept in volume between 10-400 mL. More in particular at the seeding stage the cell-culture chamber is adapted to be kept in volume between 50-100 mL.

At the cell culturing stage the cell-culture chamber is advantageously adapted to be kept in volume above 100 mL. More in particular at the cell culturing stage the cell-culture chamber is adapted to be kept in volume above 450 mL.

In an arrangement wherein the cylindrical roller is urged by compression springs acting on opposite ends of a bearing shaft, the bearing shaft is advantageously moved with respect to the first edge by at least one screw threaded spindle.

The plate member of the agitator/expansion unit is also advantageously arranged with its support surface pivotable about a substantially horizontal axis, together with the cylindrical roller positioned on top of the plate member. The means for gently agitating the cell-culture chamber then advantageously also include means for controlled rocking of the plate member. In this regard the rocking of the plate member is advantageously adapted to be carried out between angular positions of 1-90 degrees positive and 1-90 degrees negative, with respect to the horizontal. More in particular the rocking of the plate member is adapted to be between angular positions of 60-90 degrees positive and 60-90 degrees negative, with respect to the horizontal. Further it is advantageous when in each rocking cycle starts and ends with the plate member in a horizontal position. Also a rocking speed may advantageously be adapted to be optionally controlled in a variable manner, such as depending on the stage of the cell-culture process. In this regard the rocking speed for a cell-culture chamber volume of between 50 and 200 mL may advantageously be adapted to be set between 1 and 500 degrees of rotation per second A controlled rocking of the plate member is preferably adapted to be about a horizontal pivot axis extending generally perpendicular to the first and second edges of the flexible bag. During seeding the rocking rate is advantageously adapted to be kept between 1-500 degrees/second During seeding acceleration and deceleration of rocking movement is further best adapted to be kept within a range of between 1-1000 degrees/s$^2$.

Also during cell culturing acceleration and deceleration of rocking movement is preferably adapted to be kept within a range of between 1-1000 degrees/s$^2$.

Also during cell harvesting acceleration and deceleration of rocking movement is preferably adapted to be effected within a range of between 1-1000 degrees/s$^2$. Keeping within these boundaries during the entire cell culturing process helps to avoid damaging of the cells.

A bioreactor system according to the invention, may further advantageously comprise collecting means for collecting gas bubbles at the first edge of the flexible bag. Such means for collecting gas bubbles may include a relatively small headspace created in the cell-culture chamber adjacent the first edge. To this end the support for retaining the first edge of the flexible bag may advantageously be positioned perpendicular to the plate member at a vertical distance above the plate member selected in accordance with a volume of the cell-culture chamber to achieve the required removal of gas bubbles.

A bioreactor system according to the invention, may further advantageously comprise a first filter arranged to allow passage of suspension cells and for blocking passage of a plurality of microcarriers and stem cells from the third port. The anchorage dependent animal cells cultured in the bioreactor system according to the invention are advantageously mammalian stem cells. More in particular the anchorage dependent animal cells are Mesenchymal stem cells (MSC). Such stem cells for seeding may initially have been obtained from crude biopsy.

The third port of a bioreactor system according to the invention may advantageously have first and second outlets, positioned adjacent to the first fluid port.

The agitator and expansion unit of the bioreactor system of the invention is advantageously associated with further equipment operable to pump microcarriers from a microcarrier suspension vessel into the cell-culture chamber.

During the seeding stage it may be an option to add crude bone marrow aspirate to the cell-culture chamber, in conjunction with introduction of microcarriers into the cell-culture chamber.

The bioreactor system may advantageously be arranged so that waste culture medium removed from the cell-culture chamber is passed through the at least one filter having a 8-100 µm mesh size.

Further advantageous aspects of the invention will become clear from the appended description and in reference to the accompanying drawings, in which.

Figure 1:
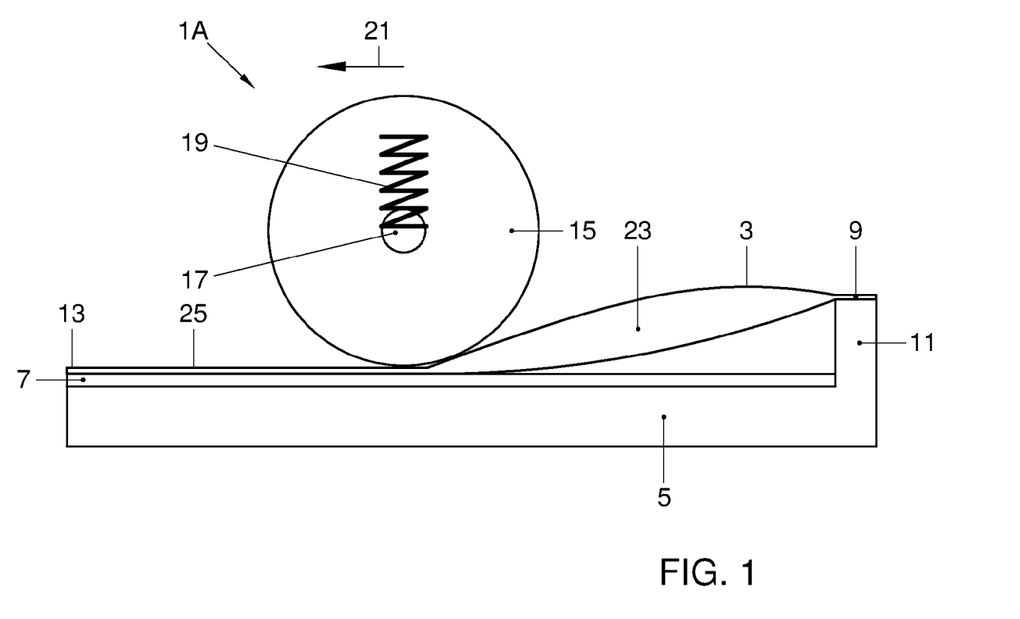
FIG. 1 is a schematic elevation of a first embodiment of a bioreactor system employing flattening of a cell-culture-bag.

In FIG. 1 a first embodiment of a bioreactor system 1A in accordance with the invention is schematically shown. A variable volume container in the form of a single use disposable bag 3 is supported on a rigid support member 5. The support member 5 has a flat upper support surface that is covered with a resiliently compressible material, such as in this example a silicon elastomeric layer 7. The bag 3 has a first edge 9 that is removably attached to a raised portion 11 at a first end of the support member 5. A second edge 13 of the bag 3 is removably attached to a second end of the support member 5 opposite the first end. A cylindrical roller 15 is arranged on second of the bag 3 for flattering the bag 3 between the roller 15 and the silicon layer 7 to reduce the variable volume of the bag 3. The roller 15 is rotably mounted on an axle shaft 17, which axle shaft is spring biased toward the support member 5 by a compression spring 19. To change the volume of the variable volume bag 3 (i.e. increasing the volume during expansion of cell growth) the cylinder 15 will be moved with its axle shaft 17 parallel to the support surface of the support member 5. The cylinder 15 will thereby move in the direction of arrow 21 starting from a position close to the raised portion 11 of the support member 5. The starting position of roller 15 close to the first edge 9 of the bag 3 is chosen such that a minimum volume area is defined within the bag 3 adjacent its first edge 9 that is appropriate for starting a cell culture. During a cell culture within the bag 3 the roller 15 will gradually move from its starting position towards the second edge 13 of the bag at the opposite end of the support member 5. As a result of the pressure exerted on the roller 15 by the spring 19 the variable volume bag 3 is clamped between the roller 15 and the support member 5 in such a way that a fluid within the bag 3 cannot escape from the compartment 23 defined between the roller 15 and the first edge 9 of the bag 3. More in particular the fluid from the compartment 23 cannot pass to a flattened section 25 of the bag 3 that extends between the roller 15 and the second edge 13 of the bag 3. The elastomeric layer 7 thereby is effective in distributing the pressure exerted by the roller 15 evenly over an adequate surface of the bag 3. This ensures that whether the roller 15 s static, or moving to increase the volume of the compartment 23, the pressure surface on the bag 3 is sufficient to prevent any fluid to move beyond the nip between the roller 15 and the support member 5.

To enhance cell growth within the compartment 23 the support member 5 together with the entire assembly can be rocked about a horizontal axis extending preferably perpendicular to the axle shaft 17 of the roller 15. This rocking motion can be carried out continuously or at intervals and can extend between 90 degrees on one side of a horizontal position to 90 degrees on an opposite side of the horizontal position. It is to be understood that different angles of rocking movement (larger or smaller than 90 degrees) or a rocking axis having a different orientation are also possible to obtain an optimal mixing of the cell culture within the compartment 23.

Figure 2:
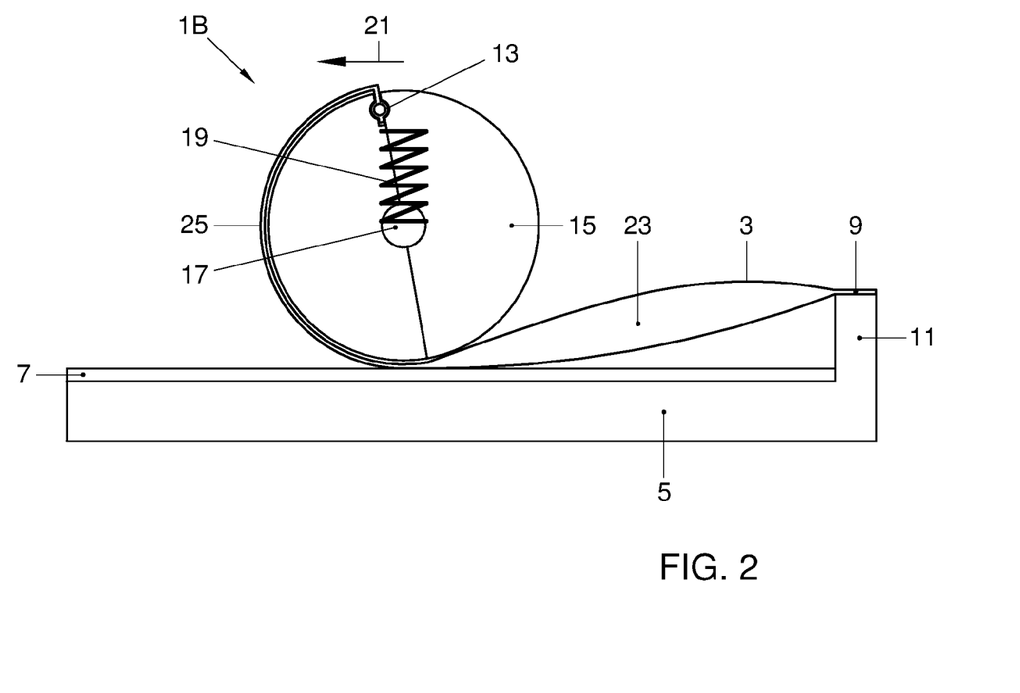
FIG. 2 is a schematic elevation of a second embodiment of bioreactor system employing winding of a cell-culture-bag.

In FIG. 2 a second embodiment of a bioreactor system 1B according to the invention is schematically shown. In this variation the second edge 13 of the variable volume bag 3 is removable attached tangentially to the roller 15. Thereby the flattened section 25 extends about a position of the perimeter of the roller 15. In FIG. 2 reference numerals have been used that are identical to those referred to above in reference to FIG. 1 and a further description of the second embodiment is thereby deemed superfluous.

Figure 3:
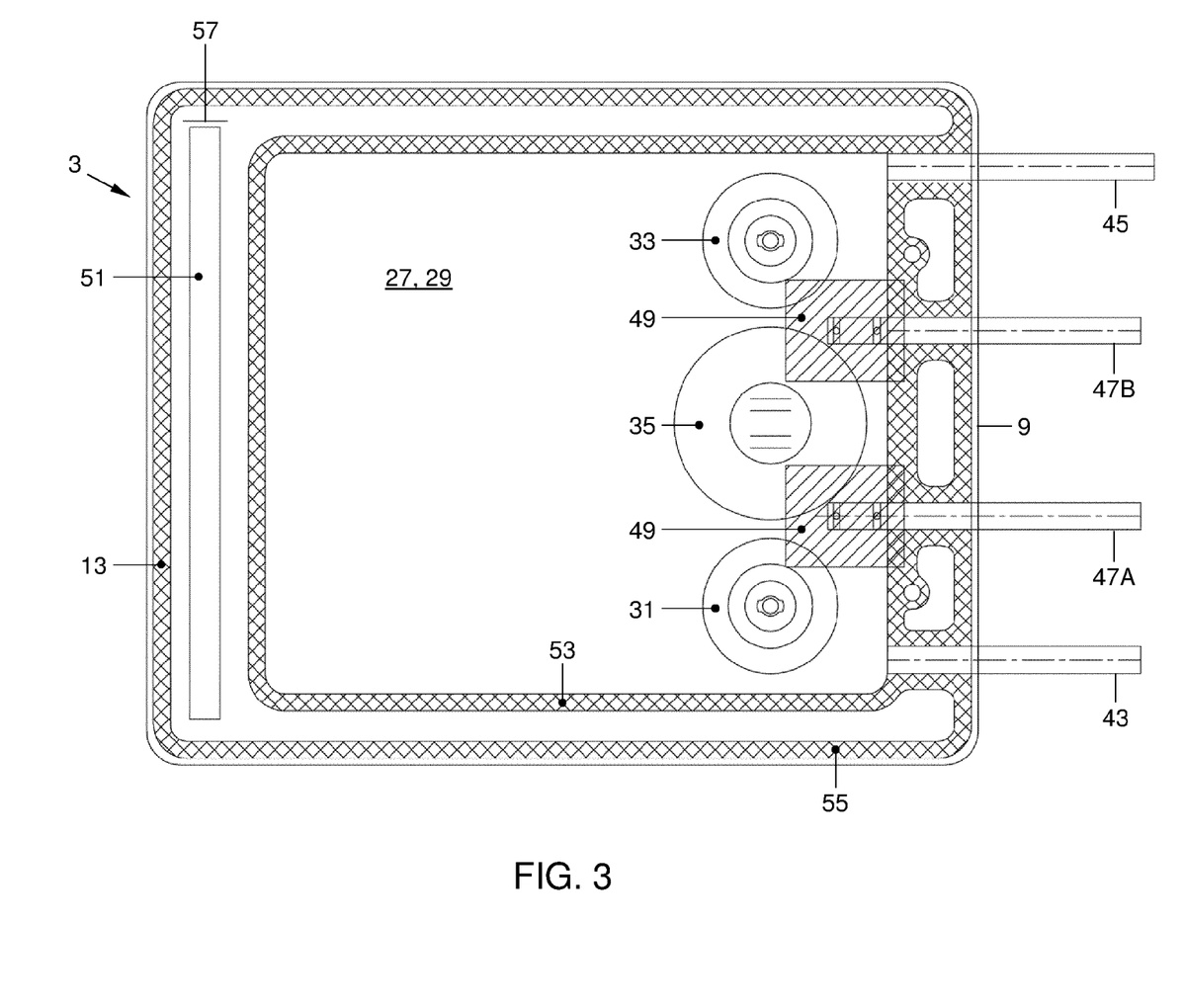
FIG. 3 is a top plan view of a transparent cell-culture-bag.
Figure 4:
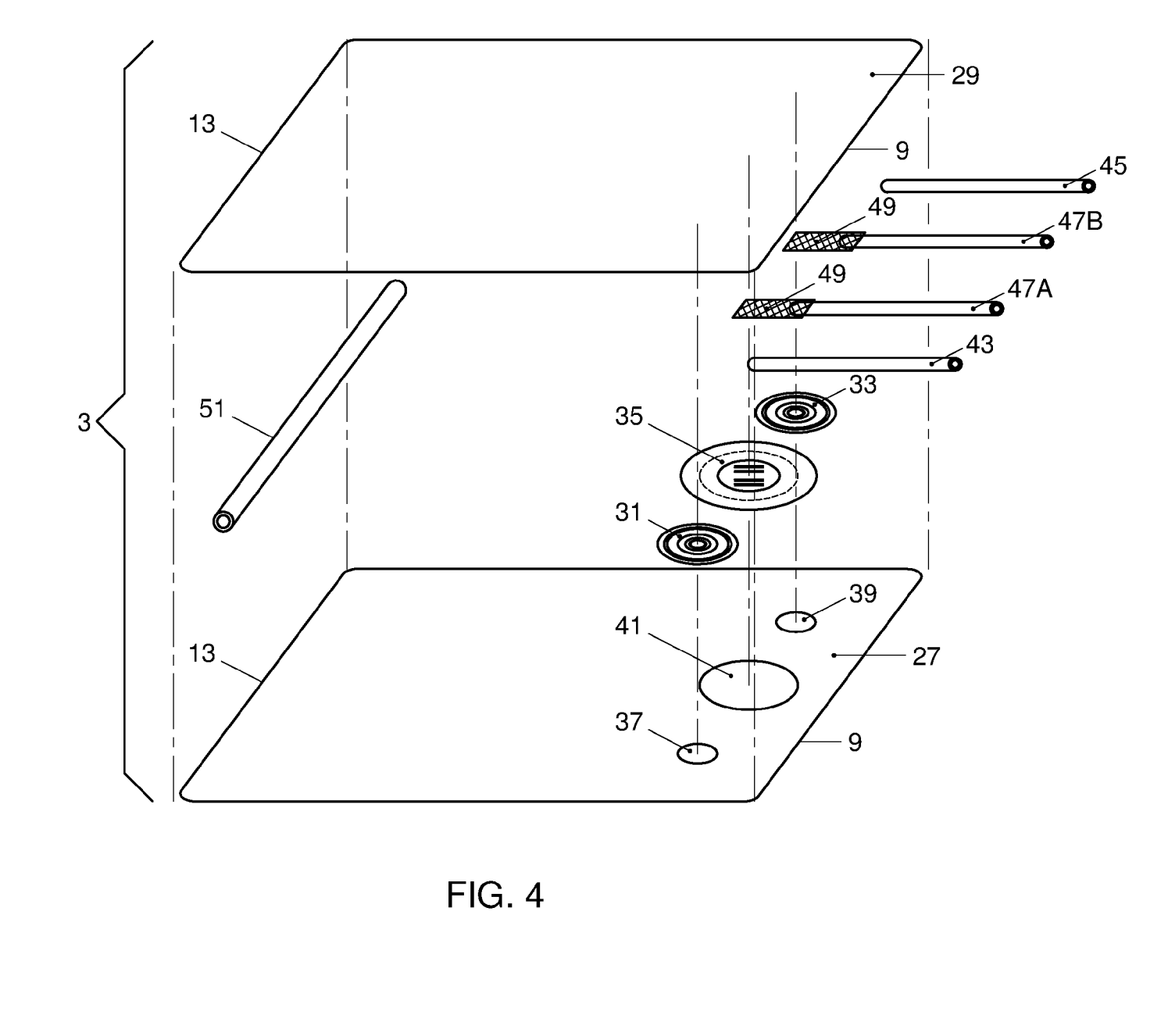
FIG. 4 is a schematic exploded view of the principal elements for making up the cell-culture-bag of FIG. 3.

The second embodiment will now be described in more detail in reference to FIGS. 3 to 9. FIGS. 3 and 4 illustrate a bag 3 that is particularly useful for use with the second embodiment 1B of the bioreactor system, but which can also be readily used, without modification, with the first embodiment 1A. As best shown in the schematic exploded view of FIG. 4 the bag 3 is composed basically of a first flexible sheet 27 and a second flexible sheet 29. These second and first sheets 29, 27 are preferably of a transparent flexible plastic foil material, such as EVE, PE, or PVC. Attached to an inside surface of the first sheet 27 are a dissolved oxygen (DO) sensor 31, a pH sensor 33, and a biomass sensor 35. The sensor for dissolved oxygen 31 and the sensor for pH 33 may be disposable fluorescent optical sensor patches, such as those supplied by Ocean Optics, 830 Douglas Avenue, Dunedin, Fla., USA or by PreSens Precision Sensing GmbH, Josef-Engert-Strasse 11, 93053 Regensburg, Germany. The biomass sensor 35 may be of a type as supplied by Aber Instruments, 5 Science Park, Aberystwyth, UK or by FOGALE nanotech, 125 rue de l'hostellerie-Bât A, 30900 Nimes, France. The sensor patches 31, 33 require an optical connection with the exterior of the bag 3 for optical excitation and detection. When the transparency of the first sheet 27 is sufficient it is simply possible to bond the sensor patches onto the interior surface of the first sheet. It is however preferred to provide openings in the first sheet 27 at the locations indicated by reference numeral 37, 39 to simplify optical connection of the respective DO and pH sensor patches 31, 33. The biomass sensor 35 uses an electrical connection to the exterior of the bag 3 and an opening 41 will also be provided in the first sheet 27 to enable the electrical connection of the biomass sensor 35.

Further sandwiched between the second and first sheets 29, 27 are a number of fluid access ports in the form of a first tubular connection 43 for adding and removing cells, microcarriers, samples from the embodiment and cell culture medium, a second tubular connection 45 for removing gas, and a pair of third tubular connections 47A, 47B for sampling fluid cell culture medium and removing liquid. To ensure that any microcarriers and adherent cells are retained in the interior of the bag 3 during sampling of the culture medium, each third tubular connection 47A, 47B is provided with a filter 49. The filter 49 has a mesh size of 60 μm and can be provided as a patch for attachment to the second sheet 29, or in the form of a pouch that is united with a perimeter seam for uniting the second and first sheets 29, 27 at the first edge 9. Also enclosed by a perimeter seam is a retaining rod 51 associated with the second edge 13 of the bag 3.

For an explanation of the perimeter seam, reference will now be made to FIG. 3, which shows a second plan view of the transparent bag 3. The first and second sheets 27, 29 of the transparent bag 3 are connected around their perimeter by an inner perimeter seam 53 defining the entire interior space and culture compartment of the bag 3, and an optional outer perimeter seam 55 for providing additional strength and rigidity to the bag 3. Further it is seen in FIG. 3 that the filters 49, here in the form of pouches, are united with the inner seam 53 at the first edge 9 of the bag 3. At the second edge 13 of the bag 3, the retaining rod 51 is encapsulated between the inner and outer perimeter seams 53, 55. While the retaining rod 51 may be positioned at the second edge 13 prior to forming thinner and outer seams 53, 55, it is also possible to provide at least one slit 57 in at least one of the first and second sheets 27, 29 so that the rod 51 can be introduced after forming of the inner and outer seams 53, 55 in the pocket thereby formed. It should further be noticed in respect of the bag 3 as shown in FIGS. 3 and 4, that it is also possible to have only a single third tubular connection instead of the pair 47A, 47B. A single third tubular connection is possible when it can be assured that a filter 49 can be provided with a sufficiently sized area, without interfering with the various sensors 31, 33, 35. In the present embodiment preference has been given to dividing the filter area between a pair of third tubular connections 47A, 47B so that these may be advantageously positioned between the sensors. It is however within the competence of the skilled person to modify this arrangement subject to requirement, as long as interference with the sensors can be avoided.

Figure 5:
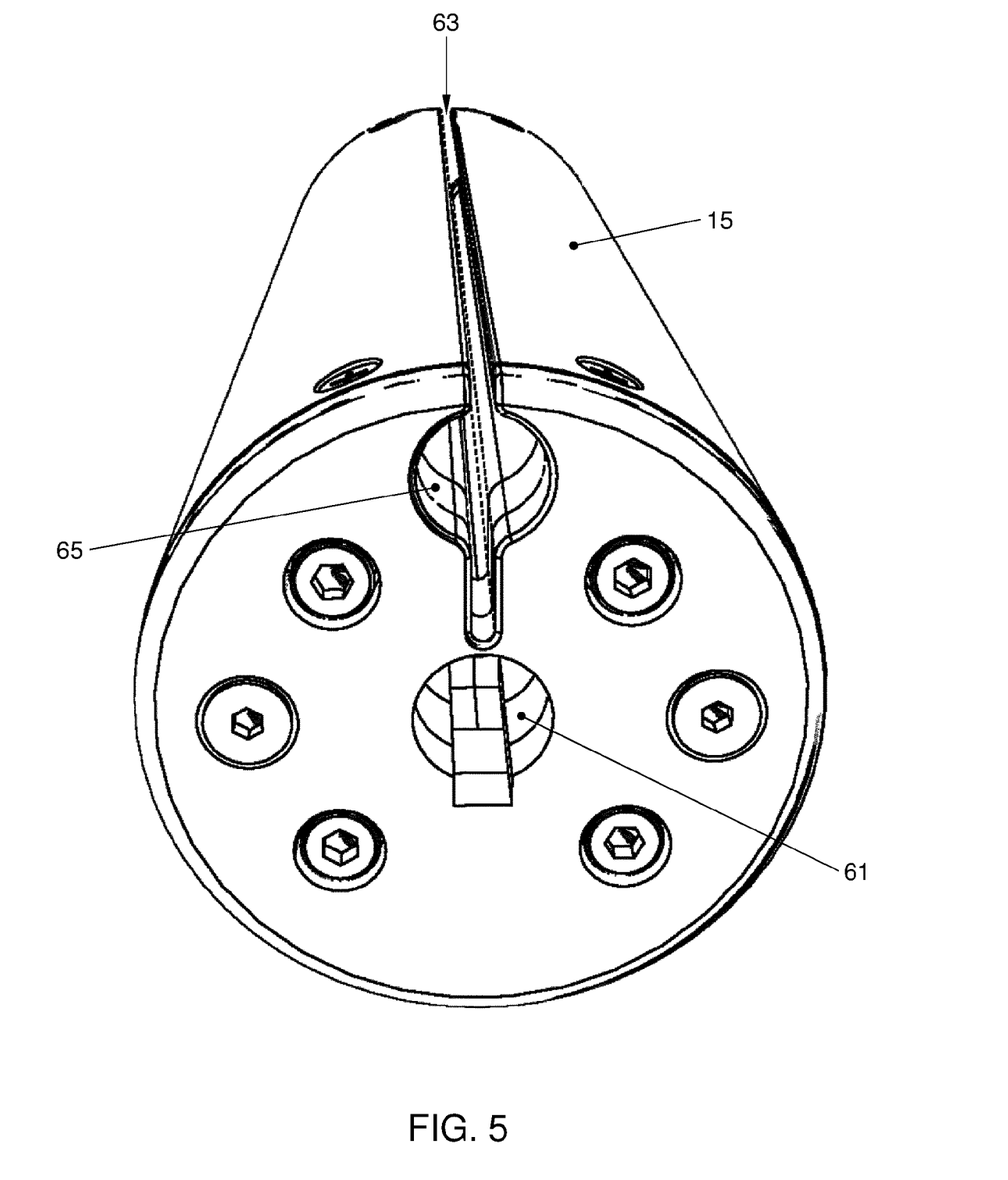
FIG. 5 is a perspective view of a cylindrical roller for use in the second embodiment of bioreactor system and alternatively is also suitable for the first embodiment.

FIG. 5, in isolation shows a perspective view of the cylindrical roller 15, which is conveniently in the form of a partly metal cylinder. To reduce the weight of the cylindrical roller 15, without compromising its rigidity, it can have a plastic (e.g. nylon), even partly hollow, core and an outer cylinder of aluminium or stainless steel or a rigid plastic. At a centre of the roller 15 an axial bore 61 is provided for the accommodation of the axle shaft 17 as schematically shown in FIGS. 1 and 2. The roller 15 is further provided with an axial slot 63 and an associated elongate cavity 65 at its circumferential perimeter for receiving the second edge 13 and the retaining rod 51 of a single use bag 3. Thereby the retaining rod 51 will be accommodated in the elongate cavity 65 and prevent the second edge 13 from slipping out of the axial slot 63.

Figure 6:
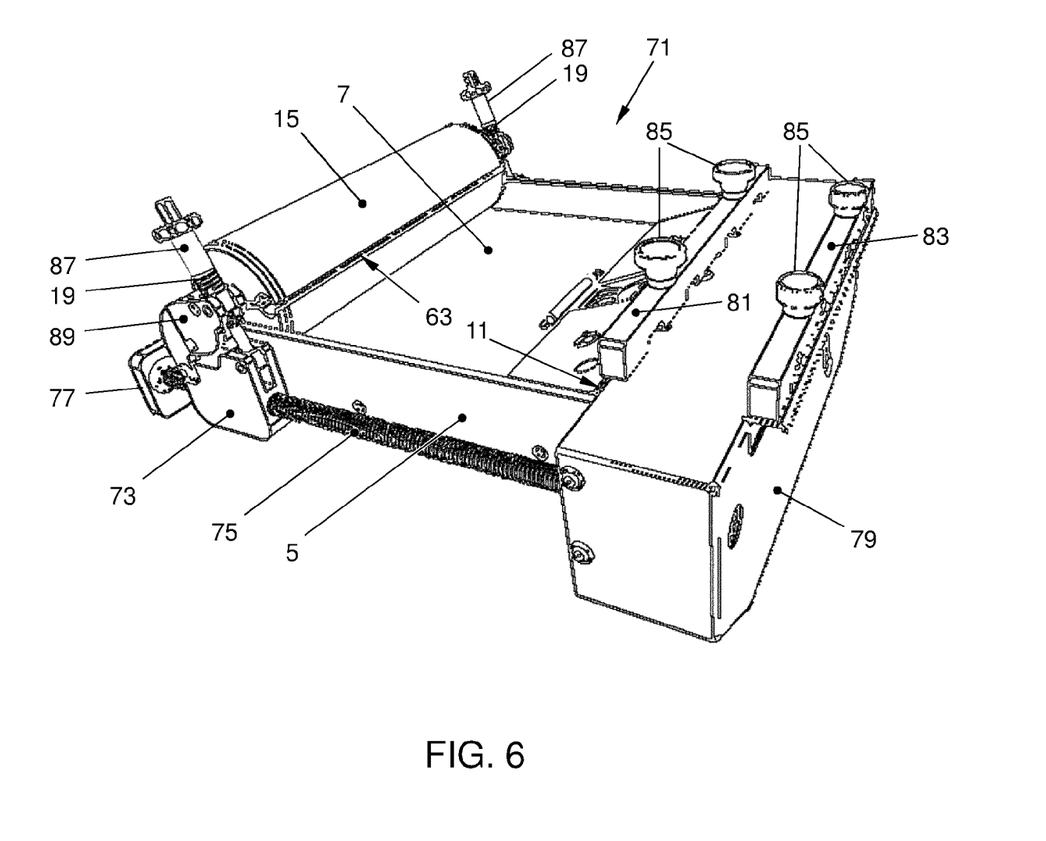
FIG. 6 is a perspective view of an agitator and expansion apparatus for use in the second embodiment of bioreactor system.

The cylindrical roller 15 in FIG. 6 is shown as part of a agitator and expansion apparatus shown without the singe-use cell culture bag for clarity in explaining the expansion system that moves the roller 15. This agitator and expansion apparatus 71, together with the cell culture bag 3, will constitute the bioreactor system 1B as schematically shown in FIG. 2. The support member 5 of the agitator and expansion apparatus 71 is tray-shaped and has a raised portion 11 on one end for attachment of a first edge (9 in FIG. 2) of the cell culture bag. A flat upper support surface of the support member 5 is formed by elastomeric layer 7. The roller 15 via its axle shaft (not visible in FIG. 6) is rotatably supported by a pair of appositely disposed carriages 73. A rotatable screw spindle 75, journalled between a bearing plate 77 and a transmission housing 79, allows controlled movement of the cylindrical roller 15 in parallel to and away from the raised portion 11. The raised portion 11 is formed to receive the transmission housing 79, which houses a driving arrangement for rotating the screw spindle 75. A similarly arranged screw spindle may be provided along the opposite side of the support member 5 to ensure the parallel movement of the roller 15 with respect to the raised portion. Nonetheless the skilled engineer can easily conceive equally effective means for translating the roller 15 parallel away from the raised portion 11. The raised portion 11 on the transmission housing 79 is further provided with a clamping bar 81 for clamping a first edge of the bioreactor of cell culture bag. A further clamping bar 83 ensures that the tubular connections of the cell culture bag can be properly held in position. Clamping screws 85 ensure that the clamping bars 81, 83 can be firmly clamped to the transmission housing 79. Screw adjusters 87 are associated with each carriage 73 on opposite longitudinal ends of the roller 15 to adjust the pressure exerted by the compression springs 19 in pressing the roller 15 against the elastomeric layer 7 of the support member 5.

Figure 7:
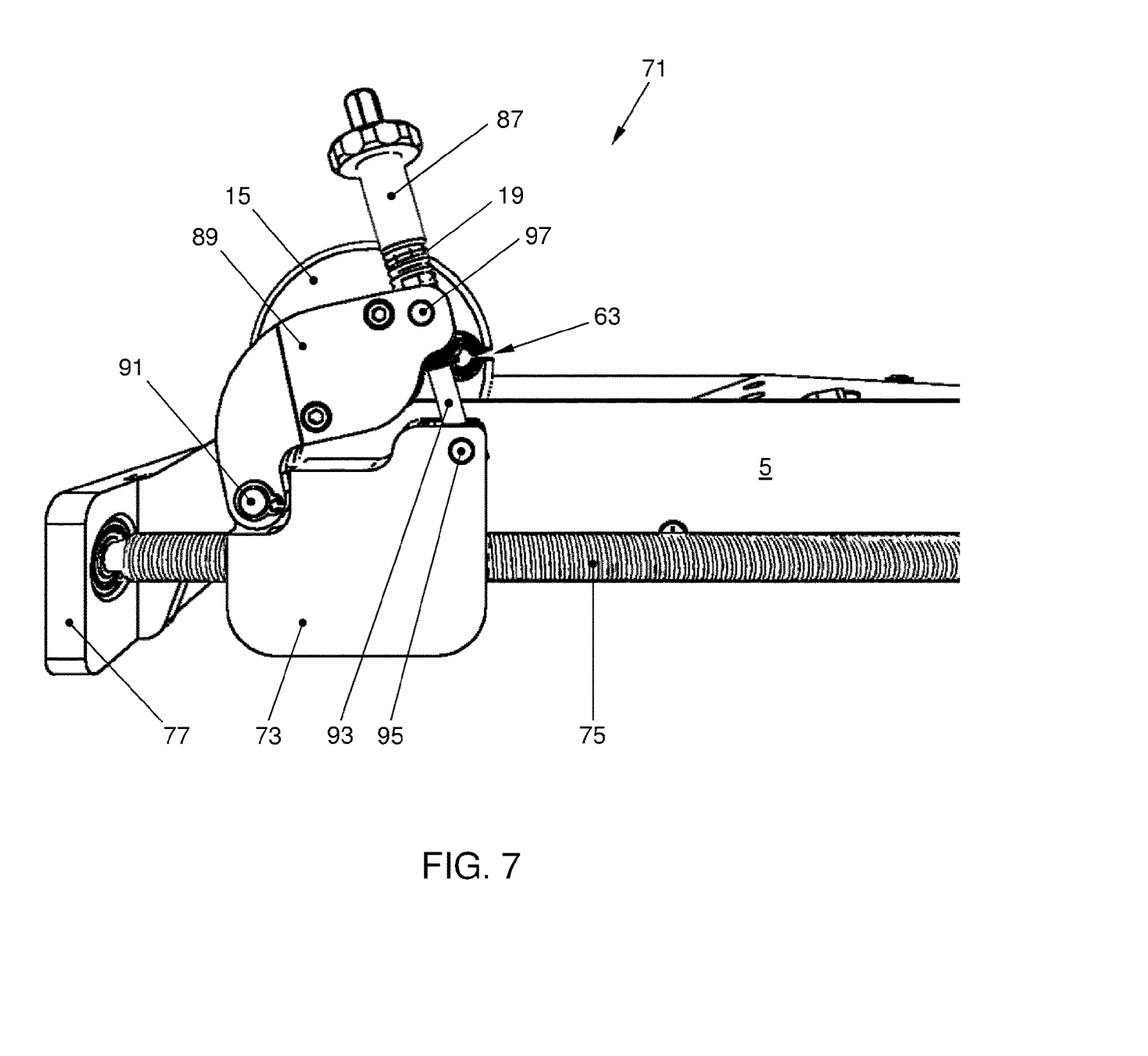
FIG. 7 shows a detail of the agitator and expansion apparatus of FIG. 6.

FIG. 7 shows an enlarged detail of the carriage 73 of FIG. 6. As best seen in FIG. 7 the carriage 73 has a roller shaft carrier 89, which is pivotally mounted thereto by a pivot pin 91. Opposite of the pivot pin 91 the screw adjuster 87 engages a screw threaded portion (not visible, but conventional) of a pillar 93 that is articulated to the carriage 73 by means of a hinge pin 95. A sliding block 97 is pivotally mounted to the shaft carrier 89 for sliding movement about the pillar 93. The screw adjuster 87 and the compression spring 19 bear against the sliding block 97 to transmit the exerted pressure to the shaft carrier 89.

Figure 8:
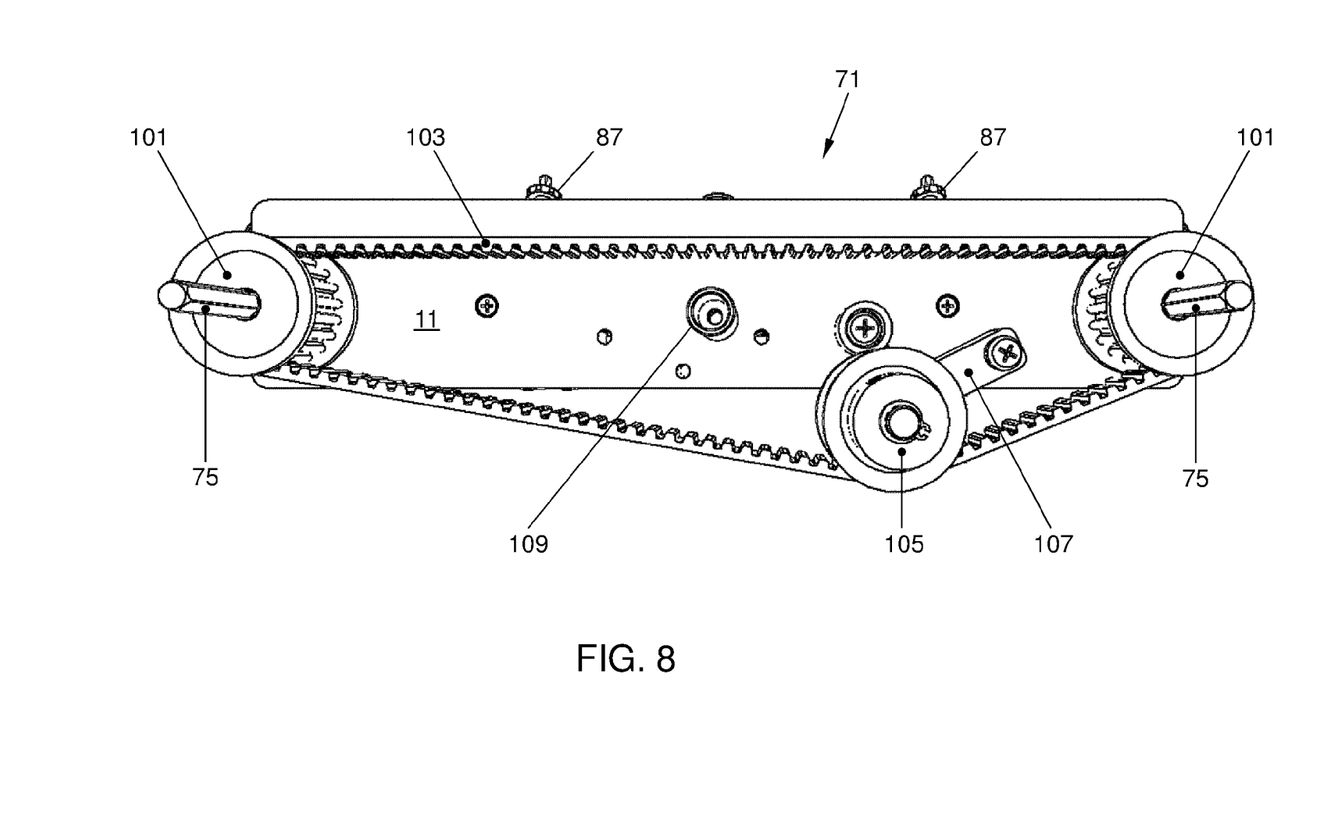
FIG. 8 is another view of the agitator and expansion apparatus of FIG. 6 with parts removed to show its drive mechanism.

FIG. 8 shows the agitator and expansion apparatus 71 from the side of the transmission housing, but with the housing 79 removed to reveal the raised portion 11 of the support member and drive means inside. As shown in FIG. 8 the longitudinal ends of the screw spindles 75 have been give a polygonal contour with flat faces, so that these ends can be engaged for rotation by toothed wheels 101. The toothed wheels 101, which have an identical diameter, are drivingly coupled with a toothed drive belt 103. The toothed drive belt 103 is kept taut by a tensioning roller 105 mounted to a free end of a pivotally mounted tensioning arm 107. The tooted belt drive ensures that both screw spindles 75 will move synchronically to move the opposite carriages (73 in FIGS. 6 and 7) at the same time along opposite sides of the support member 5. Powered drive may be introduced by electrically driving one of the exposed polygonal ends of the screw spindles 75 in any known conventional manner. It is however also possible to arrange an electric drive motor in a different position and/or to use a different mounting for the toothed wheels 101. Such modifications are considered within the capabilities of the skilled person and need no further explanation. The tensioning arm 107 may either be fixed in a pre-tensioned manner, or be spring biased. An end of a horizontal pivot axis 109 that extends perpendicular to the axle shaft 17 of the roller 15 and for rocking the support member 5 is also just visible in FIG. 8.

To ensure that the pressure exerted by the roller 15 (refer to FIG. 6) is constant across the width of the support member 5 it has proven to be sufficient to adjust each of the screw adjusters 87 with the same torque. It will be clear to the skilled person that more elaborate arrangements, such as hydraulics, can also be used to ensure that the ends of the roller shaft exert the same force on the roller 15.

Figure 9:
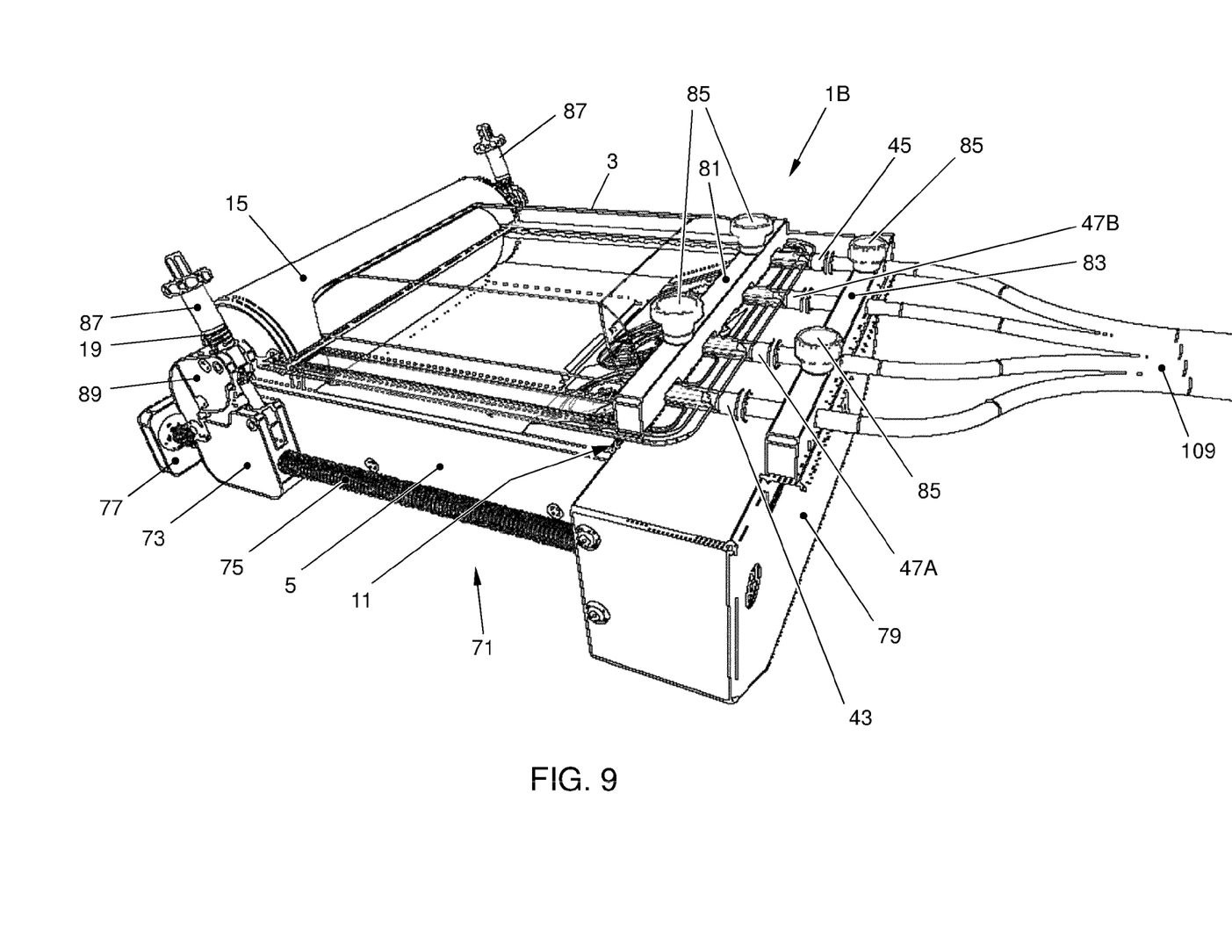
FIG. 9 is a perspective view of the bioreactor system according to the second embodiment.

FIG. 9 shows the bioreactor system 1B in its entirety with a cell culture bag installed on the support member 5 of the agitator and expansion apparatus 71. The tubular connections 43, 45, 47A, and 47B are each connected to further tubing, generally indicated by reference numeral 109, which are further connected to a perfusion unit (not shown), which may be associated with the agitator and expansion apparatus 71, for sampling the cell culture medium, for removing gas and agitating the support member 5 to keep the microcarriers with adherent cells in suspension in the culture medium and for promoting cell growth.

Accordingly a bioreactor system (1A; 1B) is disclosed for culturing anchorage dependent animal or human cells in suspension. The system (1A; 1B) includes a variable volume container (3) having a flexible outer wall (27, 29) defining a cell-culture chamber for containing a fluid culture medium, and anchorage dependent cells in suspension. The variable volume container (3) includes a first edge (9) for removable attachment to a support (5) of an agitator/expansion unit of the bioreactor system, and a second edge (13), parallel to and spaced from the first edge (9), for removable attachment to one of a cylindrical roller (15) and a support (5) of the agitator/expansion unit. A minimum volume area (23) of the container (3) defined adjacent to the first edge (9), has a first fluid port (43) in the minimum volume area (23) connectable to the agitator/expansion unit of the system for adding and removing cells, microcarriers and cell culture medium; a second fluid port (45) in the minimum volume area (23) connectable in the system for removing gas; and a third fluid port (47A; 47B) in the minimum volume area (23) connectable in the system. The variable volume container also has at least one filter (49) associated with the third fluid port (47A; 47B) to ensure that the third port enables sampling of the fluid cell culture medium while retaining any microcarriers and adherent cells in the cell culture chamber. The agitator/expansion unit of the system (1A; 1B) is in fluid communication with the first, second and third fluid ports (43, 45, 47A; 47B) for performing controlled replenishment of the culture medium in the cell-culture chamber, to admit fresh nutritive culture medium into the cell-culture chamber and for allowing draining of waste culture medium from the cell-culture chamber. The agitator/expansion unit further has the roller (15) for pinching the outer wall of the variable volume container (3) to unwind a flattened section (25) of the variable volume container.

Thereby the variable volume container increases its volume forming the cell-culture chamber, starting from the initial minimum volume area (23), and means for gently agitating the cell-culture chamber. Control means are associated with the agitator/expansion unit for periodically performing seeding, intermitted operation of the agitation and pinching means, and for harvesting, and collecting of cultured cell material.

As explained herein above the bioreactor system according to the invention includes as essential elements a single-use cell culture bag and a agitator/expansion apparatus. The single-use cell culture or bioreactor bag is made of a flexible plastic foil with tubes, filter(s) and sensors. The described example comprises two filters of 60 μm with a total area of approximately 36 cm2. The filters in the bioreactor bag are needed to keep the adherent cells on microcarriers in the bioreactor bag during perfusion of the medium. Via this outlet, used medium samples without cells can be taken. One tube is for adding cells, microcarriers and fresh medium to the bioreactor bag and take samples with microcarriers and cells from the bioreactor bag. One other tube is for removing air bubbles from the bioreactor bag. In this single-use bioreactor bag there are three sensors:

a sensor to measure pH;
a sensor to measure dissolved oxygen; and
a sensor to measure the biomass.

The biomass sensor is optional. The tubes, filters and the sensors are placed in such a way that a minimal volume of 50-150 mL is created by clamping the foil of the bioreactor bag, so a small compartment is created. The starting volume of the bioreactor bag and the perfusion tubes are small enough to keep the excreted compounds above the critical level. During cultivation of the cells, the volume can be expanded in such a way that the concentration of the excreted components stay above the critical level. The expansion can take place in discreet volume steps or stepless from 50 mL to the maximum volume.

The agitator/expansion apparatus contains a cylindrical roller, advantageously a cylinder with at least a metal or rigid plastic perimeter surface, which is pressed onto the foil material of the single-use bioreactor bag to clamp the foil and create a small volume. The bag is attached to the cylinder by pushing it in a slide. The rod of the bioreactor bag, fits in a cleft of the cylinder. The pressure is controlled by using a torque screwdriver to apply a specific pressure on the cylinder. Under the bioreactor bag a flexible sheet, preferably resiliently compressible (such as silicone elastomere) is added to make the clamping more effective. By moving the cylinder toward the end of the bioreactor bag, the volume will be increased from the smallest possible volume to the large possible volume. This expansion system moves in a rocking motion from horizontal to max 90° or −90°, to mix the culture in the bioreactor bag. The position of the installation of the bioreactor bag and the clamping is not at the same level, see FIGS. 1 and 2. This is designed this way to make it possible to collect air bubbles in one part of the bioreactor bag where the air outlet tube is positioned, if the system is positioned vertical during the rocking motion. And this installation position is needed to give the bioreactor bag space so it can expand vertical effectively to create space for the volume of the bag. In this way the shape of the bioreactor bag is like a cushion, which is the most effective volume expansion shape for the bioreactor bag.

It is thus believed that the operation and construction of the present invention will be apparent from the foregoing description and drawings appended thereto. It will be clear to the skilled person that the invention is not limited to any embodiment herein described and that modifications are possible which should be considered within the scope of the appended claims. Also kinematic inversions are considered inherently disclosed and to be within the scope of the invention. In the claims, any reference signs shall not be construed as limiting the claim. The term 'comprising' and 'including' when used in this description or the appended claims should not be construed in an exclusive or exhaustive sense but rather in an inclusive sense. Thus the expression 'comprising' as used herein does not exclude the presence of other elements or steps in addition to those listed in any claim. Furthermore, the words 'a' and 'an' shall not be construed as limited to 'only one', but instead are used to mean 'at least one', and do not exclude a plurality. Features that are not specifically or explicitly described or claimed may be additionally included in the structure of the invention within its scope. Expressions such as: "means for . . . " should be read as: "component configured for . . . " or "member constructed to . . . " and should be construed to include equivalents for the structures disclosed. The use of expressions like: "critical", "preferred", "especially preferred" etc. is not intended to limit the invention. Additions, deletions, and modifications within the purview of the skilled person may generally be made without departing from the spirit and scope of the invention, as is determined by the claims.

The invention claimed is:

1. A bioreactor system for culturing cells, the system including:
   a variable volume container;
   wherein the variable volume container comprises:
   a flexible outer wall defining a cell-culture chamber;
   a first edge for removable attachment to a support of an agitator unit of the bioreactor system;
   a second edge, parallel to and spaced from the first edge, for removable attachment to one of a cylindrical roller and a support of the agitator unit;
   a minimum volume area of the container being defined adjacent to the first edge;
   a first fluid port in the minimum volume area for adding and removing cells and cell culture medium;
   a second fluid port in the minimum volume area, the second fluid port being connectable to the agitator unit for removing gas;
   a third fluid port in the minimum volume area, and at least one filter associated with the third fluid port to ensure that the third port enables sampling of the fluid cell culture medium while retaining cells in the cell culture chamber; wherein
   said agitator unit having at least one inlet for fluid communication with the cell-culture chamber and adapted to admit fresh nutritive culture medium into the cell-culture chamber, said at least one inlet being connected to and in fluid communication with the third fluid port of the variable volume container and at least one outlet for fluid communication with the cell-culture chamber and adapted to allow draining of culture medium from the cell-culture chamber, said at least one outlet being connected to and in fluid communication with the first fluid port of the variable volume container for performing controlled replenishment of the culture medium in the cell-culture chamber;
   a mechanism for pinching the outer wall of the variable volume container to create a partially flattened section and operable for increasing the cell-culture chamber in volume by decreasing the flattened section, wherein said mechanism includes a transferable cylindrical roller arranged for rotation and for contacting a surface of the outer wall of the variable volume container, and further includes a support member defining a substantially flat support surface for supporting a portion of the outer wall surface of the variable volume container opposite to the cylindrical roller.

2. The bioreactor system of claim 1, wherein the cylindrical roller is adapted to receive and hold a portion of the variable volume container adjoining the second edge, and optionally wherein the cylindrical roller is adapted to clamp the portion of the variable volume container adjoining the second edge.

3. The bioreactor system of claim 1, wherein a plurality of microcarriers is suspended in the culture medium in the cell-culture chamber.

4. The bioreactor system of claim 1, wherein the fluid communication between the agitator unit and the cell-culture chamber is disconnectable.

5. The bioreactor system of claim 1, further comprising a headspace created in the cell-culture chamber adjacent the first edge for collecting gas bubbles at the first edge of the variable volume container, and optionally wherein the distance perpendicular to the support member at which the support for retaining the first edge of the variable volume container is positioned above the support member is selected in accordance with a volume of the cell-culture chamber effective to promote the required removal of gas bubbles.

6. The bioreactor system of claim 1, which is adapted for at least one of anchorage dependent cells, one of animal and human cells, mammalian stem cells, and mesenchymal stem cells (MSC), further comprising a first filter arranged for blocking passage of a plurality of microcarriers suspended in the culture medium and cells adhered thereto from the third port, and/or wherein cells for seeding are initially obtained from crude biopsy.

7. The bioreactor system of claim 1, wherein the variable volume container is adapted to be increased in volume upwardly from 10 mL.

8. The bioreactor system of claim 7, wherein at a seeding stage the cell-culture chamber in volume is adapted to be kept between 10-400 mL, and/or wherein at a cell culturing stage the cell-culture chamber in volume is adapted to be kept upwardly of 100 mL.

9. The bioreactor system of claim 1, wherein the cylindrical roller is adapted to be urged toward the support member to exert pressure on a portion of the variable volume container extending between the cylindrical roller and the support member.

10. The bioreactor system of claim 9, wherein urging of the cylindrical roller toward the support member is by a resilient spring, optionally wherein the resilient spring is adjustable in tension, and optionally wherein the resilient spring includes compression springs acting on opposite ends of a bearing shaft about which the cylindrical roller is arranged for rotation.

11. The bioreactor system of claim 10, wherein the resilient spring includes compression springs acting on opposite ends of a bearing shaft about which the cylindrical roller is arranged for rotation and the bearing shaft, about which the cylindrical roller is arranged for rotation, is itself arranged for controlled movement in parallel to and away from the first edge of the variable volume container for increasing the volume of the cell-culture chamber defined by the variable volume container, and wherein the bearing shaft is moved with respect to the first edge by at least one screw threaded spindle.

12. The bioreactor system of claim 9, wherein the substantially flat surface of the support member is covered by a resiliently deformable elastomeric layer on a surface facing the cylindrical roller to equally distribute pressure exerted by the cylindrical roller and to obtain an increased contact surface on the variable volume container.

13. The bioreactor system of claim 12, wherein the variable volume container is a flexible bag, and wherein the first edge of the flexible bag is attached to a support positioned at a distance perpendicular to the support member for retaining the first edge of the flexible bag in parallel to the surface of the support member, optionally wherein the second edge of the flexible bag, opposite to the first end, is held to a circumferential perimeter surface defined by the cylindrical roller, and optionally wherein the volume of the cell-culture chamber is increased by gradually unwinding the flexible bag from the cylindrical roller surface.

14. The bioreactor system of claim 13, wherein the cylindrical roller defines an axial slot in its circumferential perimeter surface for receiving the second edge, and optionally wherein the slot defines an undercut elongate chamber for receiving a rod encapsulated in a pocket along the second edge of the variable volume container.

* * * * *